United States Patent
Baker et al.

(10) Patent No.: US 6,815,533 B1
(45) Date of Patent: Nov. 9, 2004

(54) CRYOGRANULATION OF ACTIVATED PROTEIN C

(75) Inventors: Jeffrey Clayton Baker, Indianapolis, IN (US); Nancy Delores Jones, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/744,432

(22) PCT Filed: Jul. 26, 1999

(86) PCT No.: PCT/US99/16937

§ 371 (c)(1),
(2), (4) Date: Jan. 22, 2001

Related U.S. Application Data

(60) Provisional application No. 60/094,969, filed on Jul. 31, 1998.

(51) Int. Cl.[7] .................. A61K 38/00; A61K 38/48; C07K 14/00
(52) U.S. Cl. .................. 530/384; 530/407; 530/411; 530/418; 435/68.1; 514/2; 514/12
(58) Field of Search ................... 530/384, 407, 530/411, 418; 435/68.1, 64.1; 514/2, 12

(56) References Cited

U.S. PATENT DOCUMENTS

| | | | |
|---|---|---|---|
| 4,775,624 A | 10/1988 | Bang et al. | 435/226 |
| 4,992,373 A | 2/1991 | Bang et al. | 435/226 |
| 5,453,373 A | 9/1995 | Gerlitz et al. | 435/240.2 |
| 5,516,650 A * | 5/1996 | Foster et al. | 435/68.1 |
| 5,716,645 A * | 2/1998 | Tse et al. | 424/530 |
| 6,159,468 A | 12/2000 | Carlson et al. | 424/94.6 |
| 6,162,629 A | 12/2000 | Baker et al. | 435/216 |
| 6,395,270 B1 | 5/2002 | Carlson et al. | 424/97.64 |
| 6,436,397 B1 | 8/2002 | Baker et al. | 435/212 |
| 6,630,137 B1 | 10/2003 | Carlson et al. | 424/94.64 |

FOREIGN PATENT DOCUMENTS

WO    WO 97/20043    6/1997

OTHER PUBLICATIONS

Dorland's Illustrated Medical Dictionary, Twenty–fifth Edition, Publisher, W.B. Saunders, p. 897, 1974.*

Schmidt, D.J. et al., "Cryogranulation: A potential new final process for bulk drug substances," *Biopharm* (Apr. 1997): pp. 28–32.

Steiner, Stephen A., et al., Biochem. And Biophys. Res. Comm. 94(1):340–348 (1980).

* cited by examiner

*Primary Examiner*—Christopher S. F. Low
*Assistant Examiner*—Abdel A. Mohamed
(74) *Attorney, Agent, or Firm*—Danica Hostettler; Brian P. Barrett

(57) ABSTRACT

The present invention is directed at a method of processing an aqueous solution of protein C into a state suitable for storage, handling, and recovery. The present invention provides aqueous activated protein C solutions and an improved method of processing such solutions into cryogranules.

6 Claims, No Drawings

CRYOGRANULATION OF ACTIVATED PROTEIN C

This application claims priority of Provisional Application Ser. No. 60/094,969 filed Jul. 31, 1998.

This invention relates to the bulk manufacturing process of activated protein C.

Protein C is a serine protease and naturally occurring anticoagulant that plays a role in the regulation of hemostasis by inactivating Factors Va and VIIIa in the coagulation cascade. Human protein C circulates as a 2-chain zymogen which is activated in vivo by thrombin and thrombomodulin on phospholipid surfaces resulting in activated protein C (aPC). The protein C enzyme system represents a major physiological mechanism of anticoagulation.

Recombinant human protein C is generally produced by mammalian cell culture and purified by conventional chromatography techniques. When these techniques are performed at a laboratory scale, the resulting solution of aPC is readily handled and processed by standard techniques such as freeze drying. For production on a commercial scale, however, the aPC production and purification procedure generates a large volume of solution which is immediately shipped to formulation and filling operations in sterile bags. This method of handling large volumes of aPC is not desirable because the solution is neither stable nor easily dispensed. Furthermore, the necessity to handle large solutions of aPC links the schedule, scale, and site of commercial purification operations to the scale, schedule, and site of the commercial formulation fill/finish operations.

A stable preformulation form of aPC is preferred. Freeze-drying usually is a viable option for rendering a protein in a bulk biological solution in the solid form as an amorphous powder. However, amorphous proteins can be unstable for extended periods. The large volumes of solution generated in the commercial manufacturing process renders freeze drying as an impractical technique due to the expense and the extended time needed to process the solution. Additionally, the freeze-dried protein can be fluffy, dusty, and difficult to handle as an amorphous solid powder (Akers and Schmidt, *BioPharm* 10(4):29–31, 1997).

Frozen solutions of aPC are not suitable for a commercial setting because containers freeze and thaw unevenly, generating concentration gradients and autoproteolysis. Freezing of large volumes of solution requires a significant amount of time and the resulting "blocks" of frozen solution are difficult to handle. Moreover, containers of frozen aPC are not readily dispensed for filling or sampling.

Therefore, commercial production of aPC generates a large volume of a biologically active solution that is difficult to process. A stable preformulation form is preferred to facilitate handling and to maintain the product integrity of the solution during the manufacturing process. Traditional "block" freezing or commercial freeze drying procedures are not practical and do not solve this problem. Thus, there remains the need to identify a stable, preformulation form of the aPC solution generated in the manufacturing process that is suitable for storage, handling, and recovery.

The present invention provides cryogranules of activated protein C. The invention further provides a process of preparing cryogranules which comprises providing an aqueous solution of activated protein C, dividing the aqueous solution of aPC into droplets, and freezing said droplets in liquid nitrogen forming cryogranules.

The invention further provides a process of thawing the cryogranules of activated protein C, adding a pharmaceutically acceptable excipient, dispensing the solution into unit dosage receptacles, and lyophilizing the solution.

For purposes of the present invention, as disclosed and claimed herein, the following terms are defined below.

aPC or activated protein C whether recombinant or plasma derived—aPC includes and is preferably human protein C although aPC may also include other species or derivatives having protein C proteolytic, amidolytic, esterolytic, and biological (anticoagulant or pro-fibrinolytic) activities. Examples of protein C derivatives are described by Gerlitz, et al., U.S. Pat. No. 5,453,373, and Foster, et al., U.S. Pat. No. 5,516,650, the entire teachings of which are hereby included by reference.

r-hPC—recombinant human protein C zymogen, produced in prokaryotic cells, eukaryotic cells or transgenic animals.

r-aPC—recombinant human activated protein C produced by activating r-hPC in vitro or by direct secretion of the activated form of protein C from procaryotic cells, eukaryotic cells, or transgenic animals [Cottingham, WO97/20043] including, for example, secretion from human kidney 293 cells as a zymogen then purified and activated by techniques well known to the skilled artisan demonstrated in Yan, U.S. Pat. No. 4,981,952, the entire teachings of which are herein incorporated by reference.

Zymogen—refers to secreted, inactive forms, whether one chain or two chains of protein C.

Cryogranules—frozen, discrete granules from solutions or slurries of activated protein C formed after contact with a cryogenic material such as liquid nitrogen.

Pharmaceutical formulation—a formulation or solution that is appropriate to be given as a therapeutic agent.

Aqueous solution—a liquid solvent that contains water. Aqueous solutions may be comprised solely of water, or may be comprised of water plus one or more miscible solvents, and may contain dissolved solutes such as sugars or other excipients. The more commonly-used miscible solvents are the short-chain organic alcohols, such as, methanol, ethanol, propanol, short-chain ketones, such as acetone, and polyalcohols, such as glycerol.

Pharmaceutically acceptable bulking agent—agents such as but not limited to sucrose, trehalose and raffinose which provide a pharmaceutically elegant formulation which has a uniform appearance and is readily solubilized when resuspended with the appropriate solute. A pharmaceutically elegant formulation is desired for parenteral administration.

The present invention provides a process for producing cryogranules of activated protein C. Cryogranules preserve the biological activity of aPC and are suitable for storage, handling, and recovery of aPC during the manufacturing process.

Preserving the biological activity of recombinantly produced proteins during the bulk manufacturing process and bulk distribution to product manufacturing facilities is a critical issue in the biotechnology process. Unlike most bulk manufacturing processes which prepare a solid bulk distribution form, proteins produced by recombinant technology, generate large volumes of solution during the cell culture and purification process. Generally, this bulk solution must be transported to formulation and filling operations. Bulk biological solutions are often frozen because of their instability in solution at refrigerated or higher temperatures. Nonetheless, freezing is slow and nonuniform and, in some cases, causes considerable degradation which may adversely affect product quality. Freeze-thaw procedures in recombinant protein manufacturing can denature and/or inactivate many enzymes. Redissolution of frozen proteins does not always readily occur. Therefore, traditional freezing of large volumes of solutions containing recombinant proteins is not only unpredictable and generally results in a decrease in yield and a loss of activity of the protein but also results in a preformulation form that is problematic for formulation and filling operations. (Pikal, *BioPharm* 3(8):18–27, 1990; Pikal, *Biopharm* 3(9):26–30, 1990).

Proteins often present unique stability problems when traditional methods of freezing or freeze-drying are utilized. Aggregation leading to insoluble protein is a common observation which can adversely affect enzymatic activity. Furthermore, serine proteases such as aPC can autodegrade, leading to decreased functionality. Previous studies describing the production of aPC have not addressed the unique problems associated with commercial production, storage, and handling of the bulk protein substance (for example, U.S. Pat. Nos. 5,270,040, 5,550,036, 5,681,932 and Japanese patent application JP7165605). Therefore, the applicants are the first to provide a means of solving the problems of chemical and biological activity associated with the commercial production of recombinantly produced activated protein C and have discovered that cryogranulation is superior to traditional freezing or freeze-drying in producing a stable bulk protein substance suitable for storage, handling, and recovery.

Generally, the aPC solution cryogranulated as described herein comprises aPC and water. Preferably, the solution also includes other excipients including a pharmaceutically acceptable salt and a buffer. The cryogranulation solution contains up to 40 mg/ml aPC. Preferably, the cryogranulation solution contains about 1 mg/ml to about 30 mg/ml aPC. More preferably, the cryogranulation solution contains about 2.5 mg/ml to about 20 mg/ml aPC. The preferred concentration of aPC is 10 mg/ml.

Pharmaceutically acceptable salts used in the cryogranulation of aPC typically refers to a salt formed between any one or more of the charged groups in the protein and any one or more physiologically-acceptable, non-toxic cations or anions. Organic and inorganic salts include, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, carbonic, and the like, or for example, ammonium, sodium, potassium, calcium, or magnesium. The preferred salt in the present invention is sodium chloride. Preferably, the sodium chloride concentration is about 150 mM to about 1000 mM. More preferably, the sodium chloride concentration is about 325 mM to about 650 mM. The preferred sodium chloride concentration is 400 mM.

Representative buffer systems for controlling pH at a moderately acidic pH to a moderately basic pH include such compounds as phosphate, acetate, citrate, arginine, TRIS, and histidine. "TRIS" refers to 2-amino-2-hydroxymethyl-1,3,-propanediol, and to any pharmacologically acceptable salt thereof. Other buffers that are physiologically acceptable, and that are suitable for controlling pH at the desired level will be known to those of ordinary skill in the art. Preferred buffer systems include sodium citrate and sodium phosphate. The most preferred buffer is sodium citrate. The preferred molarity is about 10 mM to about 50 mM citrate. More preferably, the molarity is about 20 mM. The preferred pH is between about pH 5.0 and about pH 7.0. More preferably the pH is between about pH 5.6 and about pH 6.4. The most preferred pH is about pH 6.0.

Therefore, the excipient free solution comprising 10 mg/ml aPC, 23.4 mg/ml (400 mM) sodium chloride, and 3.78 mg/ml (20 mM) citrate, pH 6.0, was found to be optimal for cryogranulation for the commercial formulation of aPC.

Cryogranulating aPC as described herein results in a stable preformulation protein substance suitable for storage, handling, and recovery. The process is high yielding, and the product generated is not flocculent, is enzymatically stable when stored at −70° C., and is easily contained in a production setting.

The cryogranulation of aPC preferably employs a cryogranulation unit such as the 500S Cryogran Unit (IQF Inc., Ontario Canada) or other such units appreciated in the art. Optimal cryogranules are flowable, discrete frozen pellets. For example, if the droplets are too small a "spray" results in loss in yield or falling through the conveyor of the cryogranulation unit. If the drops are too large they can collide and clump forming a cryogranule "clot". Also, if the droplets are too large they do not freeze uniformly. Uniformity of the droplets and hence cryogranule size is a function of the flow rate of the process stream forming the droplets such as viscosity and/or surface tension. The preferred size of the cryogranules is about 2 mm to about 10 mm in diameter.

Cryogranules of aPC are generated by contacting droplets of aPC cryogranulation solution in liquid nitrogen or other freezing agents suitable for rapidly freezing the solution at temperatures from −40° C. to −90° C. Discrete frozen pellets of aPC are produced during the residence time in which the cryogranulation solution is in contact with liquid nitrogen. The means to contact the aPC solution and the freezing agent is not critical to the present invention. Generally, the stream of liquid nitrogen and the frozen pellets are deposited onto a mesh conveyor belt that allows the liquid nitrogen to fall through and into a collection vessel. The frozen pellets of aPC are collected, transported into an insulated container and held below the glass point of the solution.

Properly formed cryogranules can be properly handled, such as scooping, weighing and separating them. Cryogranulation of aPC significantly facilitates the manufacturing process by bridging the interface between bulk and fill/finish manufacturing operations. Thus, cryogranulation offers significant advantages over alternative procedures available for the aPC production and purification process.

Preparation 1

Preparation of Human Protein C

Recombinant human protein C (r-HPC) is produced in Human Kidney 293 cells by techniques well known to the skilled artisan such as those set forth in Yan, U.S. Pat. No. 4,981,952, the entire teaching of which is herein incorporated by reference. The gene encoding human protein C is disclosed and claimed in Bang, et al., U.S. Pat. No. 4,775,624, the entire teaching of which is incorporated herein by reference. The plasmid used to express human protein C in 293 cells is plasmid LPC which is disclosed in Bang, et al., U.S. Pat. No. 4,992,373 and Berg, et al., U.S. Pat. No. 5,661,002, the entire teachings of which are incorporated herein by reference. The construction of plasmid pLPC is also described in European Patent Publication No. 0 445 939, and in Grinnell, et al., *Bio/Technology* 5:1189–1192, 1987, the teachings of which are also incorporated herein by reference. Briefly, the plasmid is transfected into 293 cells, then stable transformants are identified, subcultured and grown in serum-free media. After fermentation, cell-free medium is obtained by microfiltration.

The human protein C is separated from the culture fluid by an adaptation of the techniques of Yan, U.S. Pat. No. 4,981,952, the entire teaching of which is herein incorporated by reference. The clarified medium is made 4 mM in EDTA before it is absorbed to an anion exchange resin (Fast-Flow Q, Pharmacia). After washing with 4 column volumes of 20 mM Tris, 200 mM NaCl, pH 7.4 and 2 column volumes of 20 mM Tris, 150 mM NaCl, pH 7.4, the bound recombinant human protein C zymogen is eluted with 20 mM Tris, 150 mM NaCl, 10 mM $CaCl_2$, pH 7.4. The eluted protein is greater than 95% pure after elution as judged by SDS-polyacrylamide gel electrophoresis.

Further purification of the protein is accomplished by making the protein 3 M in NaCl followed by adsorption to a hydrophobic interaction resin (Toyopearl Phenyl 650 M, TosoHaas) equilibrated in 20 mM Tris, 3 M NaCl, 10 mM $CaCl_2$, pH 7.4. After washing with 2 column volumes of equilibration buffer without $CaCl_2$, the recombinant human protein C is eluted with 20 mM Tris, pH 7.4. The eluted protein is prepared for activation by removal of residual calcium. The recombinant human protein C is passed over a metal affinity column (Chelex-100, Bio-Rad) to remove calcium and again bound to an anion exchanger (Fast Flow Q, Pharmacia). Both of these columns are arranged in series and equilibrated in 20 mM Tris, 150 mM NaCl, 5 mM EDTA, pH 7.4. Following loading of the protein, the Chelex-100 column is washed with one column volume of the same buffer before disconnecting it from the series. The anion exchange column is washed with 3 column volumes of equilibration buffer before eluting the protein with 0.4 M NaCl, 20 mM Tris-acetate, pH 6.5. Protein concentrations of recombinant human protein C and recombinant activated protein C solutions are measured by UV 280 nm extinction E0.1%=1.81 or 1.85, respectively.

Preparation 2

Activation of Recombinant Human Protein C

Bovine thrombin is coupled to Activated CH-Sepharose 4B (Pharmacia) in the presence of 50 mM HEPES, pH 7.5 at 4° C. The coupling reaction is done on resin already packed into a column using approximately 5000 units thrombin/ml resin. The thrombin solution is circulated through the column for approximately 3 hours before adding MEA to a concentration of 0.6 ml/l of circulating solution. The MEA-containing solution is circulated for an additional 10–12 hours to assure complete blockage of the unreacted amines on the resin. Following blocking, the thrombin-coupled resin is washed with 10 column volumes of 1 M NaCl, 20 mM Tris, pH 6.5 to remove all non-specifically bound protein, and is used in activation reactions after equilibrating in activation buffer.

Purified rHPC is made 5 mM in EDTA (to chelate any residual calcium) and diluted to a concentration of 2 mg/ml with 20 mM Tris, pH 7.4 or 20 mM Tris-acetate, pH 6.5. This material is passed through a thrombin column equilibranted at 37° C. with 50 mM NaCl and either 20 mM Tris pH 7.4 or 20 mM Tris-acetate pH 6.5. The flow rate is adjusted to allow for approximately 20 min. of contact time between the rHPC and thrombin resin. The effluent is collected and immediately assayed for amidolytic activity. If the material did not have a specific activity (amidolytic) comparable to an established standard of aPC, it is recycled over the thrombin column to activate the rHPC to completion. This is followed by 1:1 dilution of the material with 20 mM buffer as above, with a pH of either 7.4 or 6.5 to keep the aPC at lower concentrations while it awaited the next processing step.

Removal of leached thrombin from the aPC material is accomplished by binding the aPC to an anion exchange resin (Fast Flow Q, Pharmacia) equilibrated in activation buffer (either 20 mM Tris, pH 7.4 or 20 mM Tris-acetate, pH 6.5) with 150 mM NaCl. Thrombin does not interact with the anion exchange resin under these conditions, but passes through the column into the sample application effluent. Once the aPC is loaded onto the column, a 2–6 column volume wash with 20 mM equilibration buffer is done before eluting the bound aPC with a step elution using 0.4 M NaCl in either 5 mM Tris-acetate, pH 6.5 or 20 mM Tris, pH 7.4. Higher volume washes of the column facilitated more complete removal of the dodecapeptide.

The anticoagulant activity of activated protein C was determined by measuring the prolongation of the clotting time in the activated partial thromboplastin time (APTT) clotting assay. A standard curve was prepared in dilution buffer (1 mg/mL radioimmunoassay grade bovine serum albumin [BSA], 20 mM Tris, pH 7.4, 150 mM NaCl, 0.02% $NaN_3$) ranging in protein C concentration from 125–1000 ng/mL, while samples were prepared at several dilutions in this concentration range. To each sample cuvette, 50 µL of cold horse plasma and 50 µL of reconstituted activated partial thromboplastin time reagent (APTT Reagent, Sigma) were added and incubated at 37° C. for 5 min. After incubation, 50 µL of the appropriate samples or standards were added to each cuvette. Dilution buffer was used in place of sample or standard to determine basal clotting time. The timer of the fibrometer (CoA Screener Hemostasis Analyzer, American Labor) was started immediately after the addition of 50 µL 37° C. 30 mM $CaCl_2$ to each sample or standard. Activated protein C concentration in samples are calculated from the linear regression equation of the standard curve. Clotting times reported here are the average of a minimum of three replicates, including standard curve samples.

EXAMPLE 1

Production of Activated Protein C Cryogranules

A 500S Cryogran Unit (IQF Inc., Ontario Canada) is utilized for the cryogranulation of activated protein C. The 500s Cryogran Unit contains a 72 nozzle filling head with 15–18 gauge square-tipped needles, ½" long and operates at a liquid feed rate of approximately 15 ml/min per needle. A 12" wide liquid nitrogen river interfaces at the point of product entry, processing approximately 65 liters of cryoganulation solution per hour. Therefore, at 15 ml/min per needle and a 72 needle nozzle filling head, the total run time for one lot of 100 liters of solution is approximately 90 minutes. Thus, a cryoganulation solution comprised of 10 mg/ml aPC, 23.4 mg/ml (400 mM) sodium chloride, and 3.78 mg/ml (20 mM) citrate, pH 6.0, is processed in the 500S Cryogran Unit to form droplets which are frozen into cryogranules as described.

EXAMPLE 2

Stability Recombinant Human Activated Protein C

The stability of cryogranulated, recombinant human activated protein C (aPC) was monitored over a period of 34 weeks. The potency of aPC was monitored using the automated partial thromboplastin time (APTT) bioassay, and variant forms of the molecule resulting from proteolytic cleavage were monitored using the high-pressure liquid chromatography/mass spectrometry (HPLC/MS).

Cyogranulated aPC was produced as described in Example 1. These cryogranules were stored frozen at −70°

C. and samples were periodically removed for analysis. The following table indicates which of the above-mentioned procedures were used at the various time points of analysis:

TABLE 1

| Analysis Timepoint (weeks) | 0 | 22 | 28 | 29 | 33 | 34 |
|---|---|---|---|---|---|---|
| N-terminal Degradation Products | <5% * | <5 * | N/A | <5% | 6% | N/A |
| Proteolytic Cleavage Products | <5% | <5% | N/A | <5% | <5% | N/A |
| Potency | 382 U/mg | 355 U/mg | 484 U/mg | N/A | N/A | 448 U/mg |

N/A - data not available

The limit of quantitation (LOQ) for the HPLC/MS procedure is 5%, thus a value of "<5%" is below the LOQ.

There is no evidence for an overall decrease in potency of the aPC cryogranule lot during the time of storage, and the percentages of proteolytic cleavage products did not increase during the time of storage. The percentage of N-terminal degradation products has increased above the limit of quantitation for the method at the 33-week time point, but the increase is not significant. Based on these three data sets, stability of aPC cryogranules has been demonstrated over 34 weeks when stored frozen at −70° C.

We claim:

1. A method of processing an aqueous solution of human activated protein C comprising:
   dividing the aqueous solution of human activated protein C into droplets; and
   freezing said droplets into cryogranules.

2. The process of claim 1 further comprising:
   thawing human activated protein C cryogranules to form a solution
   dispensing said solution into unit dosage receptacles; and
   lyophilizing said solution.

3. The process of claim 2, further comprising adding a pharmaceutically acceptable bulking agent to said solution prior to dispensing said solution into unit dosage receptacles.

4. The process of claim 3 wherein the pharmaceutically acceptable bulking agent is sucrose.

5. The process of any of claims 1, 2, 3, or 4 wherein the droplets are frozen using liquid nitrogen.

6. The process of any of claims 1, 2, 3, or 4 wherein the cryogranules are about 2 mm to about 10 mm in diameter.

* * * * *